(12) United States Patent
Hornegger et al.

(10) Patent No.: US 8,183,529 B2
(45) Date of Patent: May 22, 2012

(54) METHOD FOR THREE-DIMENSIONAL PRESENTATION OF A MOVED STRUCTURE USING A TOMOGRAPHIC METHOD

(75) Inventors: Joachim Hornegger, Effeltrich (DE); Günter Lauritsch, Erlangen (DE); Marcus Prümmer, Buckenhof (DE); Christopher Rohkohl, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 625 days.

(21) Appl. No.: 12/378,793

(22) Filed: Feb. 19, 2009

(65) Prior Publication Data

US 2009/0214098 A1 Aug. 27, 2009

Related U.S. Application Data

(60) Provisional application No. 61/029,603, filed on Feb. 19, 2008.

(51) Int. Cl.
*G01T 1/20* (2006.01)
*G06K 9/00* (2006.01)
*A61N 5/10* (2006.01)

(52) U.S. Cl. ............... 250/363.01; 382/131; 378/65

(58) Field of Classification Search .......... 382/128–134; 600/410, 458; 250/559.03, 559.05, 559.07, 250/362, 363.01, 394, 395, 396 R; 378/23, 378/65

See application file for complete search history.

(56) References Cited

U.S. PATENT DOCUMENTS

| | | | | |
|---|---|---|---|---|
| 4,974,598 A * | 12/1990 | John | ............................ | 600/509 |
| 7,463,713 B2 * | 12/2008 | Mertelmeier | ................... | 378/22 |
| 7,711,168 B2 * | 5/2010 | Grady | ............................ | 382/128 |
| 2006/0120507 A1 * | 6/2006 | Brunner et al. | .................. | 378/62 |
| 2007/0053483 A1 * | 3/2007 | Nagata et al. | ..................... | 378/8 |
| 2008/0025590 A1 | 1/2008 | Zellerhoff | | |
| 2008/0031404 A1 | 2/2008 | Khamene et al. | | |
| 2008/0205722 A1 * | 8/2008 | Schaefer et al. | .............. | 382/128 |

OTHER PUBLICATIONS

Siemens Medical Solutions, "AXIOM Artis dFC and AXIOM Artis dBC", Brochure for r Siemens Medical Solutions, Order No. A91100-M1400-B151-1-7600, Druckzeichen CC 64151 WS 05035; Others; 2003.

M. Zellerhoff et al., "Low contrast 3D reconstruction from C-arm data", Proceedings of SPIE, Medical Imaging 2005, vol. 5745, pp. 646-655.

Lauritsch et al., "Towards Cardiac C-Arm Computed Tomography", IEEE Transactions on Medical Imaging, Jul. 2006, pp. 922-934, vol. 25, No. 7,; Others; 2006.

Prummer et al. "Cardiac C-arm CT: Efficient Motion Correction for 4D-FBP", submission to the SPIE Medical Imaging Conference, San Diego, CA, USA, Oct. 29-Nov. 4, 2006; Others; 2006.

Dijkstra, "A Note on Two Problems in Connexion with Graphs"; Numerische Mathematik 1, 1959, pp. 269-271.

(Continued)

*Primary Examiner* — Georgia Y Epps
*Assistant Examiner* — Don Williams

(57) ABSTRACT

The invention relates to a method for three-dimensional presentation of a moved structure using a tomographic method, in which a plurality of projection images are recorded from different imaging angles between a start angle with a start node point and an end angle with an end node point by an imaging unit during a number of rotation passes, with three-dimensional image data being able to be reconstructed from the projection images, with the projection images being spaced by a path or an edge. For determining the three-dimensional presentation for each angle of projection only those projection images are selected which minimize the sum of the paths or weighted edges between adjacent projection angles for a gating.

11 Claims, 4 Drawing Sheets

OTHER PUBLICATIONS

Blondel et al., "Reconstruction of Coronary Arteries From a Single Rotational X-Ray Projection Sequence", IEEE Transactions on Medical Imaging, May 2006; pp. 653-663, vol. 25, No. 5, Magazine.

Kachelrießβ et al., "Kymogram detection and kymogram-correlated image reconstruction from subsecond spiral computed tomography scans of the heart", Medical Physics, Jul. 2002, pp. 1489-1503, vol. 29, No. 7.

Lauritsch et al., "Temporal Resolution in Cardiac C-arm CT in the Presence of Variable Heart Rate", 9th International Meeting on Fully Three-Dimensional Image Reconstruction in Radiology and Nuclear Medicine 358; Others; 2007.

Shnayderman et al., "An SVD-Based Gray-Scale Image Quality Measure for Local and Global Assessment"; Image Processing, IEEE Transactions on Feb. 2006, vol. 15, Issue: 2, pp. 422-429; Others; 2006.

Klabunde, "Cardiovascular Physiology Concepts", Published by Lippincott Williams & Wilkins, 2005, ISBN: 078175030X); Others; 2005.

* cited by examiner

METHOD FOR THREE-DIMENSIONAL PRESENTATION OF A MOVED STRUCTURE USING A TOMOGRAPHIC METHOD

CROSS REFERENCE TO RELATED APPLICATIONS

The present application claims the benefit of a provisional patent application filed on Feb. 19, 2008, and assigned application No. 61/029,603. The present application also claims the benefit of a German application No. 10 2008 010 006.4 filed Feb. 19, 2008. Both of the applications are incorporated by reference herein in their entirety.

FIELD OF THE INVENTION

The invention relates to a method for three-dimensional presentation of a moved structure using a tomographic method.

BACKGROUND OF THE INVENTION

The invention relates to the 3D image reconstruction of dynamic objects from 2D projection images. The theory of image reconstruction demands a set of projection images of a stationary object over projection angles in the range of 200° (180°+cone angle). With a dynamic object an attempt is made to emulate a stationary object from said object. The imaging of the heart uses only the projection data that belongs to the heart phase during which the heart is practically at rest. This occurs in the end systole and in the end diastole.

Usually the heart phases are known from the EKG. The heart phase is specified relative to the heartbeat length between two QRS complexes (R wave) between 0 and 100%. The end systole is then located at around 30%, the end diastole at 70-90% for a heart rate of 60 bpm.

This is described for example in US 2008/0025590 A1 with reference to a method for temporal and three-dimensional presentation of a periodically changing structure, for example a heart, in which a number of rotation images are created. The rotation passes required are started offset by a specific angle for an identical event of the periodic process, initiated by the specified event in the EKG signal. New image series are assembled from the rotation images, with 3D image presentations able to be reconstructed for different phase areas of the period.

As an alternative there is the kymogram method in CT imaging, as is described by Kachelrieβ Et al. in "Kymogram detection and kymogram-correlated Image reconstruction from subsecond spiral computed tomography scans of the heart", published in Med. Phys. 29(7), pages 1489 to 1503, July 2002. The kymogram method determines the focal point in the projection images and searches for phases with a focal point that remains the same. For the kymogram method the projection images must be complete in the transaxial direction. This however is not the case with C-arm computer tomography.

SUMMARY OF THE INVENTION

The object to be achieved by the invention is to develop the above method so that a heart phase suitable for gating can be found even without recording an EKG.

A plurality of projection images are recorded from different imaging angles between a start angle with a start node point and an end angle with an end node point by an imaging unit during a number of rotation passes. Three-dimensional image data is able to be reconstructed from the projection images. The projection images are spaced by a path or an edge.

The object is inventively achieved, for determining the three-dimensional presentation, by selecting only those projection images for each projection angle which minimize the sum of the paths or weighted edges between adjacent projection angles for a gating.

It has proved advantageous if, for three-dimensional presentation of each projection angle with node point, only that projection image is selected in which among the set of the possible paths or edges the sum of the paths or weighted edges between adjacent node points possesses the lowest measure of distance.

Inventively the method can have the following steps:
a) Recording the image data by a number of rotation passes,
b) Preprocessing the image data recorded,
c) Determining the average heart rate,
d) Measuring the distances of the heart rates from the average heart rate,
e) Determining edge weights,
f) Determining the projections along of the shortest path or edge between the start node point and the end node point,
g) Reconstructing the 3D data set and
h) Presenting the 3D data set.

Advantageously the average heart rate can be computed in an image-oriented manner, with it being determined in accordance with step c) and e) using the Euclidean distance method.

Inventively the shortest distance of the paths in accordance with steps e) and f) can be determined using the Dijkstra algorithm.

It has proved advantageous for the preprocessing in accordance with step b) to contain the following steps:
S1 Preprocessing of 3D reconstruction algorithms,
S2 Reduction of the image data,
S3 Lowpass filtering,
S4 Computing the size of the image gradient (optional) and/or
S5 Formation of a Region Of Interest (ROI).

In this case the step S1 can inventively include x-ray scatter correction, beam hardening correction, truncation correction, overradiation correction, a correction of the low frequency drop and/or a correction of the ring artifacts.

BRIEF DESCRIPTION OF THE DRAWINGS

The invention is explained below in greater detail on the basis of the exemplary embodiments shown in the drawing. The figures are as follows.

DETAILED DESCRIPTION OF THE INVENTION

Figure 1:
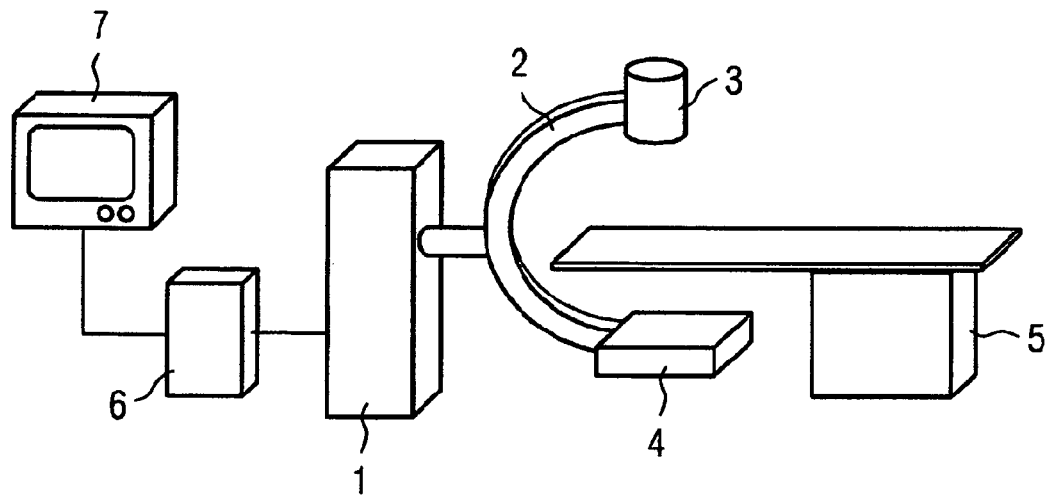
FIG. 1 a known x-ray C-arm system for carrying out the inventive method.

US 2006/0120507 A1 discloses this type of x-ray diagnostic device for executing the method for angiography which is shown for example in FIG. 1, which features a C-arm 2 supported to allow it to rotate on a stand 1, at the ends of which an x-ray radiation source, for example an x-ray emitter 3, and an x-ray image detector 4 are arranged.

The x-ray image detector 4 can be a rectangular or square flat semiconductor detector, which is preferably made of amorphous silicon (a-Si).

In the optical path of the x-ray tube assembly 3 is a patient support table 5 for recording images, of a heart of a patient to be examined for example. Connected to the x-ray diagnostic device is an imaging system 6 which receives and processes the image signals of the x-ray image detector 4. The x-ray images can then be viewed on a monitor 7.

Figure 2:
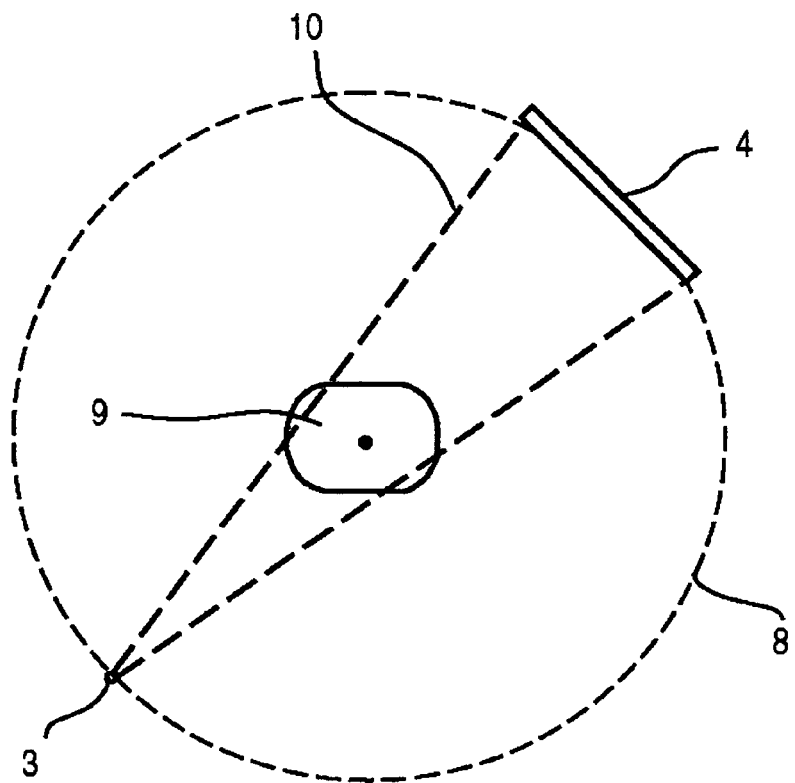
FIG. 2 a view of the track of a detector and a radiographic source in accordance with FIG. 1 around an object to be examined in the axial direction of view, FIG. 3 a diagram of a projection graph for a rotation image recorded by means of the x-ray C-arm system in accordance with FIG. 1, FIG. 4 a diagram of the relative heart phase of a forwards/backwards pass, FIG. 5 the normalized curves of the phase distance between EKG-based heart phases of a forwards/backwards pass and the image-based distance value FIG. 6 a flowchart of the inventive method and FIG. 7 a flowchart of an inventive preprocessing method.

If 3D data sets are to be created, the rotatably-supported C-arm 2 with x-ray source 3 and x-ray detector 4 is turned so that, as shown schematically in FIG. 2 looking down from above on the axis of rotation, the x-ray source 3 depicted in this diagram by its beam focus 3 as well as the x-ray image detector 4 move on a planetary track 8 around an object 9 to be examined. The planetary track 8 can be followed completely or partly for creating a 3D data set.

The object 9 to be examined can for example be the body of an animal or a human being, but can also be a phantom body.

The x-ray source 3 emits a ray bundle 10 emanating from the ray focus of its radiographic source, which hits the x-ray image detector 4.

The x-ray source 3 and the x-ray image detector 4 thus each circulate around the object 5, so that the x—ray source 3 and the x-ray image detector 4 lie on opposite sides of the object 9 in relation to each other.

In normal radiography or fluoroscopy using such an x-ray diagnostic device the medical 2D data of the x-ray image detector 4 will be buffered in the imaging system 6 if necessary and subsequently reproduced on the monitor 7.

Generally a gating is a selection of projection images. In the present case exactly one projection image is selected for each recorded image position, so that from a number of data sets a complete data set is obtained for a reconstruction.

Image guidance during interventional heart examinations using a cardio C-arm CT-system is desirable for many methods. The application of electrocardiogram gating during the acquisition of multiple, serial, backwards and forwards EKG-triggered rotation passes using a C-arm system allows the 3D+t reconstruction of the heart. The process of retrospective gating is an especially important component of 3D reconstruction. It allows the creation of a projection data set of the heart in a quasi-static state. The gold standard in gating is EKG-based. The EKG signal measures the electrical activity during of the heart cycle which can be correlated with a heart phase. The correlation between EKG-based and the actual heart state (heart geometry, blood volume, etc.) is very good and reliable for resting and regular heartbeats. With variable, high or abnormal heart rhythms, as frequently occur in a clinical environment, the correlation will be weaker. Therefore alternate gating methods must be sought which are based on the acquired projection data. In addition said methods can also take account of non-heart movements, such as the breathing for example, which are not accessible via the EKG. The object of the invention is to provide an image-based gating method without EKG which can utilize the already acquired projection data of a multiple rotation pass for a reconstruction.

The gating problem is represented by a weighted and directed graph of which the elements are the projection images. Each path in this graph corresponds to a possible gating. In this approach a shortest path is sought which optimizes a target function. The path outlay (weighting) is defined by similarities of projection images based on image dimensions. The optimization is additionally regulated to give preference to solutions in which consecutive selected projections are short along a C-arm pass recorded forwards or backwards. This regulation depends on an estimated average heart rate which has likewise been estimated during the image-based method. It can be shown that the introduced image-based gating method is an alternative to EKG gating.

For the present method it is assumed that no EKG signal is present and the recorded projection data has already been preprocessed, as will be described in greater detail below. Thus for example intensity variations, triggered by possible illumination controls, can have been corrected. Possible procedural sequences are for example sampling with multiple rotation passes of 6×4s or 4×4s, which for example produce six or four consecutive forwards and backwards passes of respectively approximately four seconds and approximately K=191 projections $p_i$ per pass. However other procedural sequences for recording the necessary data are likewise possible.

The forming or formulation of image-based gating is undertaken using the following intuitive observation.

For the sake of simplicity only two random 2D projections $p_1$ and $p_2$ are observed from two consecutive projection directions vi (for example $p_1 \in V_i$, $p_2 \in V_{i+1}$. The change of the image content between $p_1$ and $p_2$ is relatively small, compared to all projections from every other direction of projection. Therefore the definition of a meaningful distance value $d(p_1, p_2)$ is desirable. The computation of this distance value $d(p_1, p_2)$ is preprocessed for each projection in a number of steps. The processing steps can include: Lowpass filtering, selection of a Region of Interest (ROI) around the heart (usually the heart is centered in the projection), a local contrast enhancement or a gradient computation. Different distance functions, such as for example the sum of the quadratic difference or the correlation coefficient, are conceivable. In the present case a structure-based correlation is undertaken which provides safe results and is quick to compute. The sinogram movement (image change by detector rotation) between such consecutive projections $p_1 \in V_i$ and $p_2 \in V_{i+1}$ (inter view) is very small and a sinogram movement between two projections of the same image angle (intra view), for example $p_l \in V_i$ and $p_k \in V_{i+1}$ is not present (ignoring narrow transformations brought about by calibration).

This enables the definition of a distance value which is independent of angle to be avoided, which is a far greater problem. The projection pairs characterize the most similar heart phases if d is especially small. This idea can be expanded in order to cover all K available projection directions. Let a random set $p_1, \ldots, p_k$ of projections be recorded from consecutive projection directions $V_1, \ldots, V_k$. The degree of dissimilarity d is the sum of all $d(p_i, p_{i+1})$ for each consecutive pair of projection directions. Each possible set of projections represents a possible gating. A gating is sought which minimizes $\hat{d}$, so that theoretically the image data set is obtained which has the most similar heart phases which are contained in the data record. An efficient computation scheme for the minimization problem can be achieved by a vector representation of the ideas presented in a directed, weighted graph G=(U, E). The set of node points U contains all possible projection images and an additional start node point α and end node point ζ. The set of edges E contains an edge of all projection pairs from consecutive projection directions; edges from start node point α to the projection of V1 and edges from the projection $v_k$ to the end node point ζ. Each edge is weighted by $d(p_1, p_2)$ if the linked node points are projection images, or a constant c, if $p_1$=α or $p_2$=ζ. For a given projection graph G the optimum gating corresponds to the projection along the shortest path from the start node point α and the end node point ζ.

Figure 3:
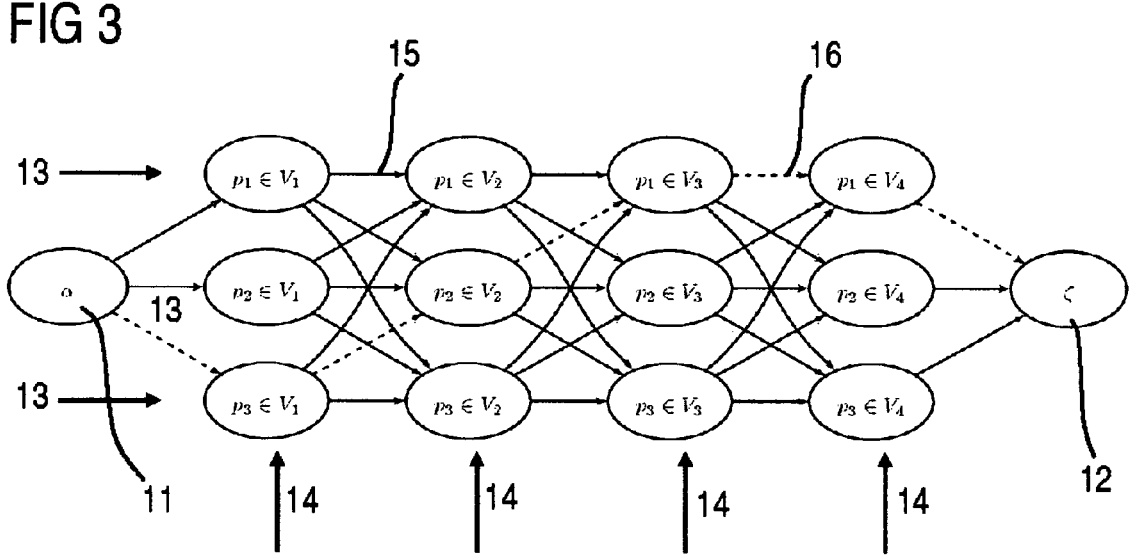

FIG. 3 shows a very narrow projection graph without weighting. It is similar to an acquisition method of three short rotation passes 13 ($p_i$) over four projection angles 14 ($V_i$). The arrows shown in the projection graph represent possible paths between the individual node points. The dashed-line paths 16 give an example for a possible gating in the projection graph shown which was determined on the basis of determining the shortest path 16.

Figure 4:
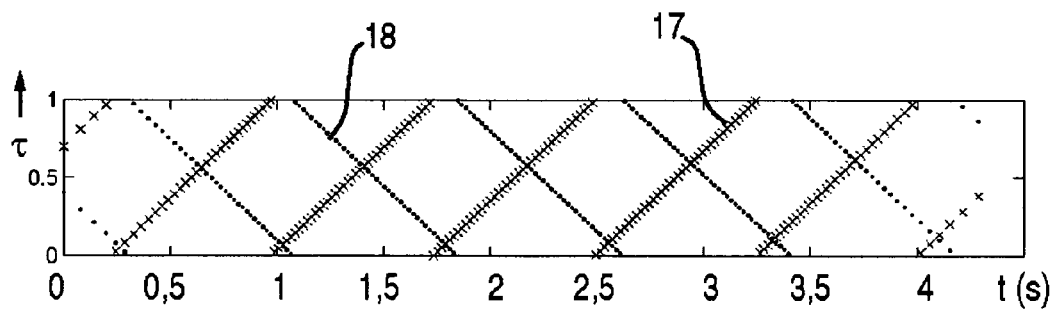
Figure 5:
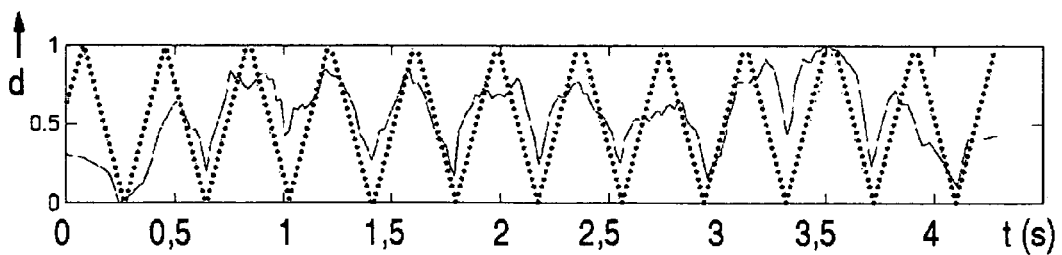

In addition a regulation of a subpath length is introduced in order to prevent a consecutive subpath of the same pass becoming too long. While the time distance between consecutive recorded projections is known the subpath length can be limited in accordance with the time. Therefore an additional outlay of a path is added if consecutive parts of a selected path along the same pass exceed a certain part of a predicted average heartbeat duration. In order to obtain the average heart rate based on images, the following method is employed:

A forwards pass is observed in which the C-arm rotates from an angle 1 ... N and pauses for a certain time. Then the backwards pass is started and projection images are now collected in the reverse arrangement of the angles N ... 1. If the heart phase distances are now considered at each angle 1 ... N over time, a number of minimum values are produced, which are shown in FIG. 5. The forwards pass 17 is identified by the crosses x and the backwards pass 18 by the dots •. In FIG. 4 the lines of the forwards and backwards passes cross. Evidently these minimum values correspond to crossing points of the heart phase; for example both images show the same heart phase. Luckily this situation can be exploited by an image-based algorithm which only determines the distance between image projection pairs of the same angulation. With a predetermined set of minimum values between all combinations of the Intra-projection direction of forwards and backwards passes as reference, an optimization procedure can be started. It demands an artificial heart signal over the duration of the recording which corresponds to the set of minimum reference values. The optimization is undertaken in a two-step method in order to reduce the search area. First a constant heart rate is assumed and a graphic presentation of the angulation produced is shown in FIG. 5 which makes possible a comparison of the temporal position of the crossing points with the minimum value of the image-based similarities. Subsequently each heartbeat duration is modified in a stochastic gradient decrease by modification of the heart signal until a minimal temporal distance of all heartbeats between all forwards/backwards passes produces crossings.

The change of the image content for adjacent C-arm angulations is made up of the image changes as a result of the detector rotation (sinogram movement) and the changes in the heart phase. Between adjacent angles of view the distribution of the sinogram movement is to be viewed as constant and is therefore independent of the C-arm passes 1 to K. By contrast the heart phase depends on the individual pass. In each pass the object to be examined is likely to be in a different heart phase. Therefore it can be deduced from this that the similarity between consecutive C-arm angulations should have been minimized, so that the images represent the same physiological heart phase.

These considerations lead to the following algorithm:
Find a gating for the sum of the image-based distances d between adjacent projection directions in accordance with the following equation:

$$G_{IB} = \arg_{(g_1,\ldots,g_N)}^{min} \sum_{n=1}^{N-1} d(p_n^{g_n}, p_{n+1}^{g_{n+1}})$$

This formulation can also be interpreted in one term; reduce the sum of the first gradient of the heart movement which is close to zero and represents the same heart phase. This object can easily be achieved by mapping the minimization tasks as follows onto a directed graph which is called the projection graph G=(V, E):

The set of node points contains two connections or terminals α and ζ and the projection images, for example. $v=\{p_1,\ldots,p_{NK}, \alpha, \zeta\}$. The set of edges E is formed by addition of edges of the source or the start node point α to the images of the first projection view $V_1$. An edge is then added for each image of the kth projection view $v_k$ to all images of the k+1th projection view $v_{k+1}$. The images of the last projection view are connected to the end node point ζ. The directed edges are weighted by an image dimension d for each of the two projection images and if one of the node points is not a projection image (a terminal α or ζ), by a constant of c=1.

FIG. 3 shows the result of the projection graph for a very small artificial scan. The projection images along each path which connects the two terminals α and ζ is a possible gating. The shortest path between them minimizes the total of the distances between adjacent projection directions. An efficient algorithm for the shortest path problem in a circuit-free directed graph with non-negative edge weightings is known from E. W. Dijkstra, "A Note on Two Problems in Connexion with Graphs" in Numeric Mathematics 1, pages 269 to 271. This algorithm produces the dummy code of a change which contains simple subpath conditions, as will be described below.

For optimum efficiency of the projection graph a few other items of information known in advance are also considered. At first the angle increase of consecutive angulations should be small; otherwise the sinogram movement dominates and the heart phase change becomes negligible. Furthermore data inconsistencies of consecutive C-arm-passes can additionally disturb the already described relationship and dominate the changes in the image content. Further factors to be considered are noise, the dynamics of the contrast medium and non-heart movements. This will be taken into account by the preprocessing and by the introduction of gating restrictions described below.

Figure 6:
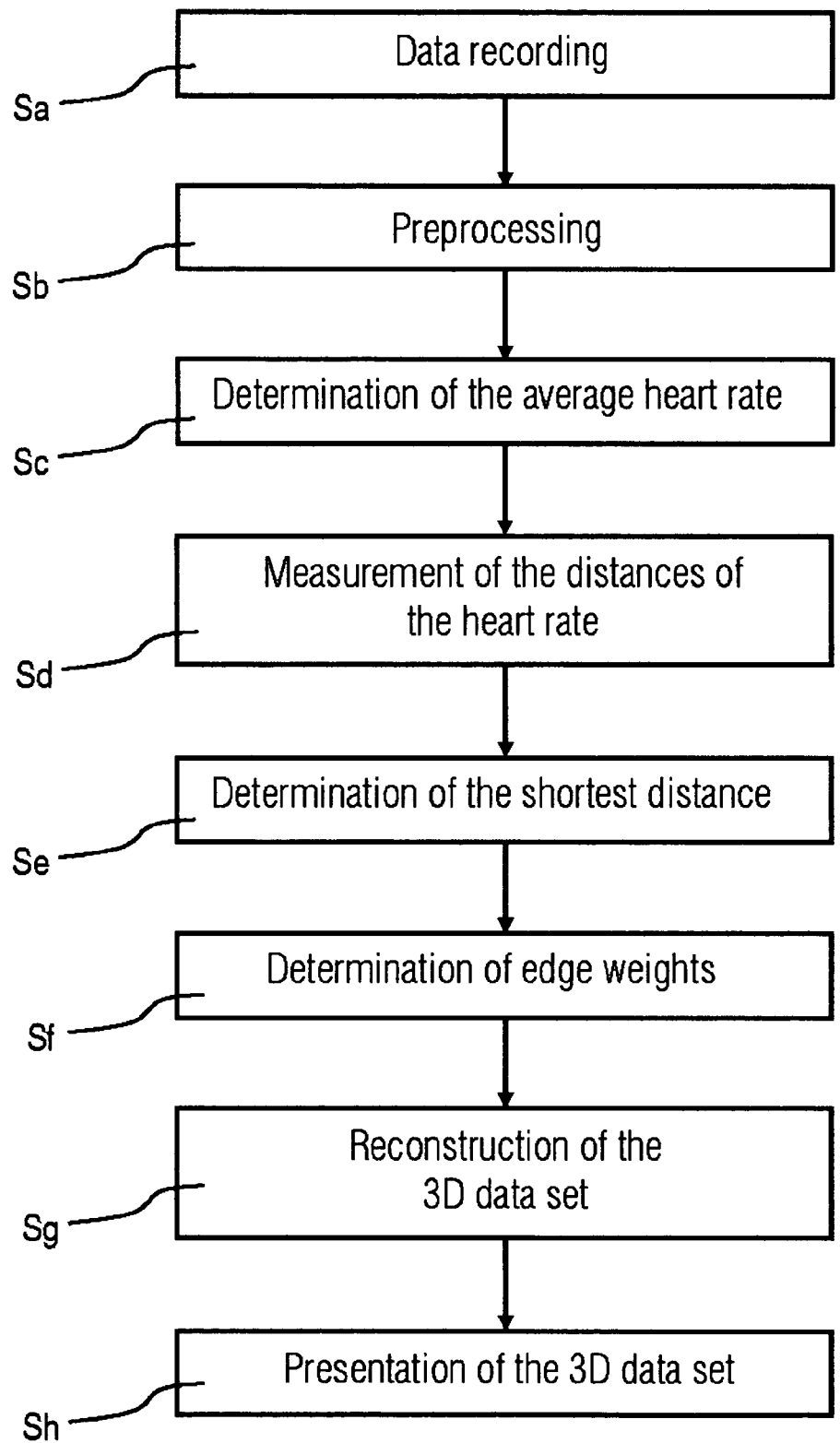
Figure 7:
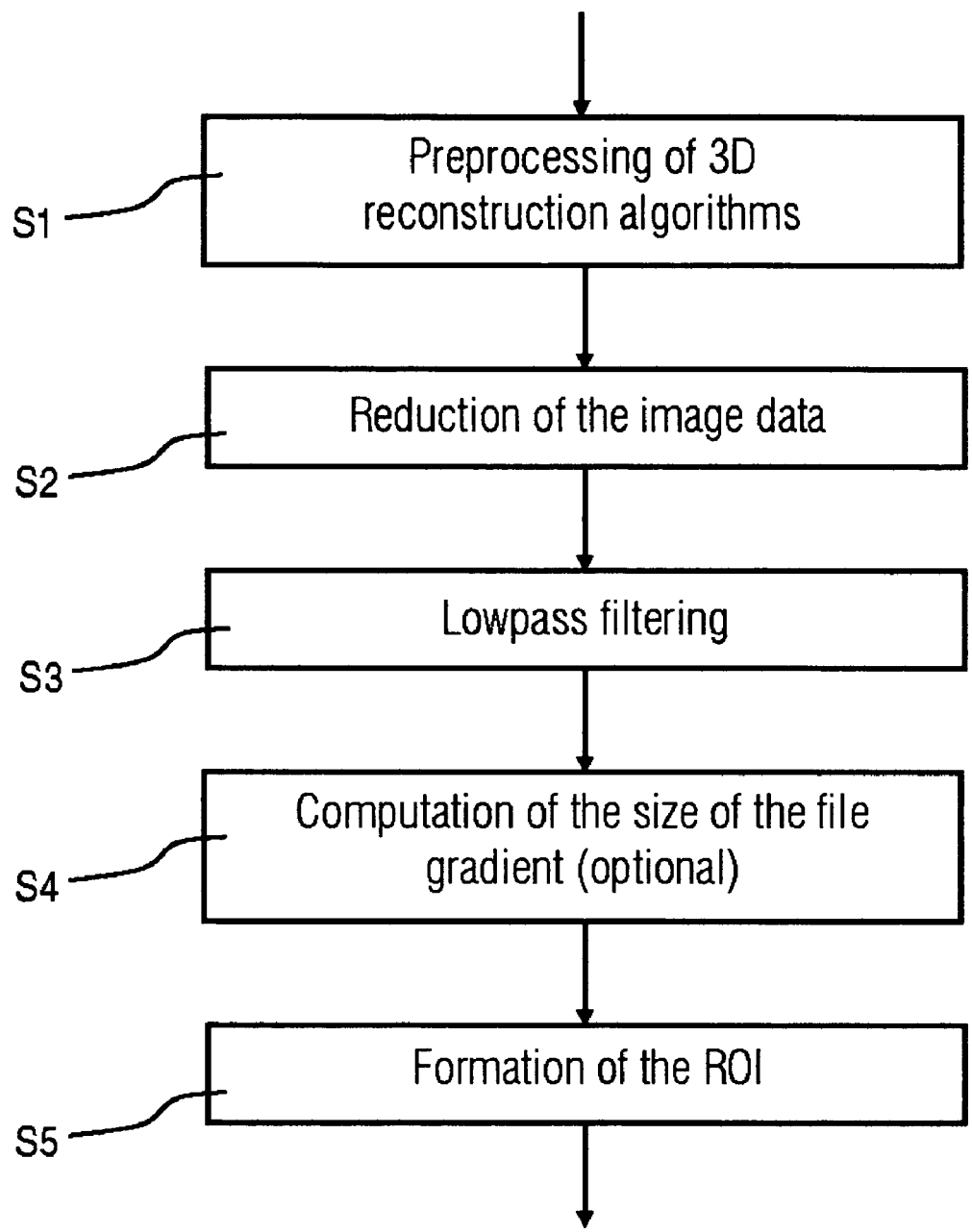

In accordance with the previous paragraphs the projection data is to undergo preprocessing. In such cases the following processing steps in accordance with FIG. 6 can be performed for a projection image:

S1 Preprocessing of 3D Reconstruction Algorithms
  Carrying out preprocessing of 3D reconstruction algorithms and selection of the images which make a direct contribution to the computation of the 3D volume. This preprocessing can generally include, but is not restricted to the correction algorithms for scattered radiation, beam hardening, truncation, overradiation, low frequency drop and ring artifacts, as is described for example in Zellerhoff Et al. in "Low contrast 3D reconstruction from C-arm data", Proceedings of SPIE, Medical Imaging 2005, Vol. 5745, pages 646 to 655, or US 2006/0120507 A1.

S2 Reduction of the Image Data
  The computation can be speeded up in this way.

S3 Filtering
  Because of the detector rotation between adjacent angle positions common structures, such as edges for example, do not overlap exactly. To compensate for this influence lowpass filtering, for example a Gauss filter kernel, is applied.

S4 Computing the Size of the Image Gradient (Optional)
  The image gradient supplies structural information about the heart geometry.

S5 Forming a Region of Interest (ROI)
  The sinogram movements extend over the complete projection image. To reduce this influence the projection images are truncated to a region of interest (ROI) required by the user so that they contain the complete heart in all projection images and heart phases.

In general any grayscale measured values can be used as distance measured value d in the image-based gating algorithm. In the present case for example three different distance measurements, the Euclidean distance, the correlation coefficient and an SVD-based measurement, which is described in A. Shnayderman, A. Gusev, and A. Eskicioglu, "An svd-based grayscale Image quality measure for local and global assessment," IEEE Transactions on Image Processing 15, pages 422 to 429, February 2006, are used. The Euclidean distance is viewed as especially advantageous because of safe and stable results with low computing effort.

To further improve the gating result, a regulation of the length of consecutive, selected projections from the same C-arm pass in a specific period is introduced. This period depends on the average heart rate which is also based on estimated image information provided. Therefore the option is introduced of performing a simple restricted, shortest-path search using the Dijkstra algorithm. In each step of the Dijkstra path search, for each possible subpath taking into account an additional validation value v, the current path outlay is added to. The algorithm produces the dummy code of the modified path search. The only change to the standard algorithm is in the line 17 and 18 of the appended program code, in which the validity value v is replaced by a function "Validity". The validity value is zero for valid gatings and infinite for non-valid gatings. A path is valid if, within of a time frame of w, no more than m projection images of an individual pass were selected. This allows the selection of only possible solutions in respect of the characteristic of the heart cycle. It is known from "Cardiovascular Physiology Concepts" by Richard E. Klabunde, Lippincott Williams & Wilkins, July 2004, (http://www.cvphysiology.com) that specific heart phases have a specific maximum period which is forced by the introduced validity value, i.e. cannot be exceeded.

Experience shows that the average heart rate $\hat{H}$ and the average time $\Delta T$ between two consecutively recorded projection images give a good intuition of how the validity parameters m and w can be parameterized. The average heart rate allows an upper limit for the diastolic or systolic period. The following heuristic values can be used for gating and have proved to be advantageous:

$$w = 0.65 \cdot \frac{1}{\hat{H}}, \quad m = \frac{w}{\Delta T}$$

This makes it possible for no more than 65% of the projections during a part of 65% of the time of a heart cycle to be selected from a single pass. The average heart rate is patient-specific and needs a derivation of the image data for a pure image-based algorithm. A method for determining the image-based mean heart rate will be described below.

During a forwards pass the C-arm rotates from an angle 1 to N and then pauses for a certain time. The backwards pass is then started and images are collected again, which are now recorded in the reverse order at the angles N to 1. The diagram in FIG. 4 shows the EKG-measured heart phases, plotted over the acquisition time. At a constant heart rate two intersection points per heart cycle can typically be observed. Shown as a dotted line in FIG. 5 is the normalized EKG distance between pairs of projection images for the same angulation. The distance for two projections P1, P2 is produced by $\min_{c \in \{0,1,-1\}} |\tau(p_1) - \tau(p_2) + c|$. The extended curve in FIG. 5 shows the normalized image-based distance measurement value d for the same pair of projection images. It is clearly evident from this that the set of times in which the heart phase of a combination of forwards and backwards passes is the same corresponds to a minimum of the image-based distance function. The core idea of the present image-based algorithm for estimated average heart rate is to create an artificial heart signal which features the same set of intersection points. This algorithm operates as follows:

Let L in the following scenario be the number of the forwards and backwards combinations (F/B combinations) In a first phase of the algorithm the image-based distance curve is determined for each of the L F/B combinations. For each of the curves the set of the local minima $R_i$ is detected. The set of all combinations $\Re = \{R_1, \ldots, R_L\}$.

In the second phase of the algorithm an artificial heart signal with an assumed constant heart rate h is created. Through this a graphical representation can be created for each F/B combination with the artificial heart signal, similar to that shown in FIG. 4. Next the minima $A_h = \{A_1^h, \ldots, A_L^h\}$ for each of the F/B combinations are computed by determination of the heart phase intersection points in the artificial signal.

For a quality measurement the match between $\Re$ and each $A_h$ is determined; a function $\lambda_M(x)$ will be introduced, which for each set of the minima M of $\Re$ or $A_h$ creates a triangular form. It assumes the value one if x is a minimum, and the value zero if x lies in the middle between two consecutive minima and a linear interpolation value for intermediate values. Expressed in visual terms, this function is a triangle with the height 1, centered around each minimum value. Using $\lambda_M(x)$ we can define the following target function to be minimized:

$$\in (h) = \sum_{i=1}^{L} \int (\lambda_{R_i}(x) - \lambda_{A_i^h}(x))^2 dx$$

which measures the quadratic difference between the reference and the artificial triangle functions of the minima for all combinations of the forwards/backwards passes. $\in$ is minimized by discretizing the search area $[h_{min}, h_{max}]$ and conducting a complete search. The optimum heart rate h will be interpreted as the average heart rate. In order to stabilize the estimated average heart rate a certain part of the best optimized heart rate is averaged. The estimated average heart rate can be further improved by an explicit change of the heart signal to minimize $\in$.

In cardiac C-arm computer tomography a number of C-arm rotations are recorded in turn (DynaCT Cardiac ECG-gated protocol). The inventive method of selecting suitable heart phases with an image-oriented method achieves the result of enabling a suitable heart phase to be found for a gating even without recording an EKG. For N C-arm rotations N projection images are recorded for each projection angle. A gating is determined which minimizes the sum of the differences of the projection images from consecutive projection angles. As an ancillary condition the mean heart rate is computed in an image-oriented manner and accordingly a timely switch in the selection of the C-arm rotations is promoted.

The EKG-based selection method can lead to an incorrect selection of projection images. The relative heart phase primarily does not yet provide any information about the movement state of the heart. The phases of relative rest during given fixed heart rates are known from experience. In the clinical environment the heartbeat length varies widely however. Within 20s a patient heart rate of between 50 bpm and 120 bpm can be observed. The heart is described in a model manner so that the systole occurs in a relatively constant predetermined absolute time. The variance in the heart rate is largely brought about by a lengthening or shortening of the diastolic phase. Thus the same relative heart phases are shown the same states of the heart.

A model-based access would have the disadvantage of not taking account of patient-dependent variations. An image-based selection variant is independent of basic assumptions. It searches out on the basis of existing projection recordings the phases of relative heart rest.

The image-based selection of the heart phases in the cardiac 3D imaging from projection images, enables 3D images of heart phases to be obtained even retrospectively without executing an EKG with less movement and thus with less unsharpness.

The typical algorithm, which determines the shortest path in the projection graphs, described in E. W. Dijkstra, "A Note on Two Problems in Connexion with Graphs" in Numerische Mathematik 1, pages 269 to 271 is reproduced in modified form G=(V, E) below. The function "getpath" generates the shortest path by means of iteration by mapping the predecessor P. The function "validity" produces the validity value for a subpath (subpath).

```
 1: P ← ∅ // Determine the predecessor of each node point which is to be
reached on the shortest path to this node point.
 2: D_s(s) ← 0            // Determine the effort for reaching a node
                             point from the source.
 3: Q ← V                 // Set of node points to be checked
 4: for all u ∈ V to which u ≠ s applies do
 5:     D_s(u) ← +∞
 6: End for
 7: while Q ≠ ∅; do
 8:     find u ∈ Q such that D_s(u) = min_{u'∈Q}(D_s(u'))
 9:     Q ← Q | u
10:     for all neighbors v ∈ Q of u do
11:         if u = s or v = t then
12:             a ← 1
13:         else
14:             a ← d(u, v)
15:         end if
16:         subpath = getpath(p, u) ∪ v
17:         if D_s(u) + a + validity(subpath) < D_s(v) then
18:             D_s(v) ← D_s(u) + a + validity(subpath)
19:             P(u) = v
20:         end if
21:     end for
22: end while
23: return      getpath(P; t)
```

The invention claimed is:

1. A method for a three-dimensional presentation of a cyclically moved bodily structure of a patient using a tomographic method, comprising:
   recording a plurality of projection images of the bodily structure of the patient from different projection angles between a start angle with a start node point and an end angle with an end node point by an imaging unit during a plurality of rotation passes, wherein the bodily structure is at least subject to movement in correspondence with a sequence of dynamically changing phases of the bodily structure;
   spacing the projection images from each other by paths;
   selecting the projection images that minimize a sum of the paths between adjacent projection angles to locate at least a point in time effective to perform an imaging-based gating for each of the projection angles; and
   reconstructing the three-dimensional presentation of the bodily structure based on the selected projection images.

2. The method as claimed in claim 1, wherein the sum of the paths between adjacent projection angles possesses a smallest measure of distance among a set of possible paths.

3. The method as claimed in claim 1, further comprising:
   preprocessing the recorded projection images,
   determining an average heart rate of the patient,
   measuring distances of heart rates from the average heart rate,
   weighting the paths,
   summing the weighted paths between the start node point and the end node point,
   selecting the projection images along a shortest weighted path among the sums of the weighted paths between the start node point and the end node point,
   reconstructing the three-dimensional presentation based on the selected projection images, and
   presenting the three-dimensional presentation.

4. The method as claimed in claim 3, wherein the average heart rate is determined based on the projection images.

5. The method as claimed in claim 3, wherein the average heart rate is determined using Euclidean distance method.

6. The method as claimed in claim 3, wherein the shortest weighted path is determined by Dijkstra algorithm.

7. The method as claimed in claim 3, wherein the projection images are preprocessed by:
   preprocessing a three-dimensional reconstruction algorithm,
   reducing image data of the projection images,
   lowpass filtering the image data,
   computing a size of an image gradient of the filtered image data, and
   creating a region of interest.

8. The method as claimed in claim 7, wherein the preprocessing of the three-dimensional reconstruction algorithm is selected in the group consisting of: an x-ray scatter correction, a beam hardening correction, a truncation correction, an overradiation correction, a correction of a low frequency drop, and a correction of a ring artifact.

9. The method of claim 1, wherein the cyclically moved bodily structure of the patient is the heart of the patient.

10. The method of claim 1, wherein the cyclically moved bodily structure of the patient is the heart of the patient and further wherein the image-based gating is configured to locate a temporal cross-over between successive phases of a cardiac cycle without use of an electrocardiogram (EKG)-based gating signal.

11. A method for a three-dimensional presentation of a cyclically moved bodily structure of a patient using a tomographic method, comprising:
- recording a plurality of projection images of the bodily structure of the patient from different projection angles between a start angle with a start node point and an end angle with an end node point by an imaging unit during a plurality of rotation passes, wherein the bodily structure is at least subject to movement in correspondence with a sequence of dynamically changing phases of the bodily structure;
- spacing the projection images from each other by edges;
- selecting the projection images that minimize a sum of the edges between adjacent projection angles to locate at least a point in time effective to perform an image-based gating for each of the projection angles; and
- reconstructing the three-dimensional presentation of the bodily structure based on the selected projection images.

* * * * *